United States Patent
Krull et al.

(10) Patent No.: US 8,720,257 B2
(45) Date of Patent: May 13, 2014

(54) METHODS, SYSTEMS AND APPARATUS FOR DETECTING MATERIAL DEFECTS IN COMBUSTORS OF COMBUSTION TURBINE ENGINES

(75) Inventors: Anthony Wayne Krull, Anderson, SC (US); Dullal Ghosh, Orissa (IN); Saurav Dugar, West Bengal (IN); Tejas Bharat Shinde, Maharashtra (IN); Gilbert Otto Kraemer, Greer, SC (US)

(73) Assignee: General Electric Company, Schenectady, NY (US)

( * ) Notice: Subject to any disclaimer, the term of this patent is extended or adjusted under 35 U.S.C. 154(b) by 668 days.

(21) Appl. No.: 12/987,340

(22) Filed: Jan. 10, 2011

(65) Prior Publication Data
US 2012/0176248 A1 Jul. 12, 2012

(51) Int. Cl.
*G01M 15/14* (2006.01)

(52) U.S. Cl.
USPC ...................................... 73/112.01

(58) Field of Classification Search
USPC ................ 73/112.01, 112.03, 112.05, 118.03
See application file for complete search history.

(56) References Cited

U.S. PATENT DOCUMENTS

| | | | |
|---|---|---|---|
| 4,573,123 A | 2/1986 | Rosenbush et al. | |
| 6,278,374 B1 | 8/2001 | Ganeshan | |
| 6,512,379 B2 | 1/2003 | Harrold et al. | |
| 6,887,069 B1 | 5/2005 | Thornton et al. | |
| 7,123,031 B2 | 10/2006 | Twerdochlib | |
| 8,475,110 B2* | 7/2013 | Hefner et al. | 415/1 |
| 2002/0116985 A1 | 8/2002 | Henning et al. | |
| 2004/0056654 A1 | 3/2004 | Goldfine et al. | |
| 2012/0067716 A1* | 3/2012 | Buske | 204/164 |
| 2012/0177491 A1* | 7/2012 | Kraemer et al. | 416/1 |

OTHER PUBLICATIONS

Search Report and Written Opinion from FR Application No. 1250251 dated Jun. 4, 2013.

* cited by examiner

*Primary Examiner* — Eric S McCall
(74) *Attorney, Agent, or Firm* — Mark E. Henderson; Ernest G. Cusick; Frank A. Landgraff

(57) ABSTRACT

A method for detecting defects in a combustion duct in a combustion system of a turbine engine while the turbine engine operates, wherein the combustion duct comprises an inner surface, which, during operation, is exposed to the hot-gas flowpath, the method comprising the steps of: providing a first electrode that is electrically connected to the combustion duct; providing a second electrode that resides within the hot-gas flowpath; applying a voltage across the first electrode and the second electrode; and detecting current flowing between the first electrode and the second electrode.

20 Claims, 6 Drawing Sheets

METHODS, SYSTEMS AND APPARATUS FOR DETECTING MATERIAL DEFECTS IN COMBUSTORS OF COMBUSTION TURBINE ENGINES

BACKGROUND OF THE INVENTION

This present application relates generally to methods, systems, and apparatus for detecting defects, including surface defects, which may occur in industrial manufacturing processes, engines, or similar systems. More specifically, but not by way of limitation, the present application relates to methods, systems, and apparatus pertaining to the detection of defects that form on the components, such as those found within the combustor, exposed to the hot-gases of combustion turbine engines.

In operation, generally, a combustion turbine engine may combust a fuel with compressed air supplied by a compressor. As used herein and unless specifically stated otherwise, a combustion turbine engine is meant to include all types of turbine or rotary combustion engines, including gas turbine engines, aircraft engines, etc. The resulting flow of hot gases, which typically is referred to as the working fluid, is expanded through the turbine section of the engine. The interaction of the working fluid with the rotor blades of the turbine section induces rotation in the turbine shaft. In this manner, the energy contained in the fuel is converted into the mechanical energy of the rotating shaft, which, for example, then may be used to rotate the rotor blades of the compressor, such that the supply of compressed air needed for combustion is produced, and the coils of a generator, such that electrical power is generated. During operation, it will be appreciated that components exposed to the hot-gas path become highly stressed with extreme mechanical and thermal loads. This is due to the extreme temperatures and velocity of the working fluid, as well as the rotational velocity of the turbine. As higher firing temperatures correspond to more efficient heat engines, technology is ever pushing the limits of the materials used in these applications.

Whether due to extreme temperature, mechanical loading or combination of both, component failure remains a significant concern in combustion turbine engines. A majority of failures can be traced to material fatigue, which typically is forewarned by the onset of crack propagation. More specifically, the formation of cracks caused by material fatigue remains a primary indicator that a component has reached the limit of its useful life and may be nearing failure. The ability to detect the formation of cracks remains an important industry objective, particularly when considering the catastrophic damage that the failure of a single component may occasion. Such a failure event may cause a chain reaction that destroys downstream systems and components, which require expensive repairs and lengthy forced outages.

One manner in which the useful life of hot-gas path components may be extended is through the use of protective coatings, such as thermal barrier coatings. In general, exposed surfaces are covered with these coatings, and the coatings insulate the component against the most extreme temperatures of the hot-gas path. However, as one of ordinary skill in the art will appreciate, these types of coatings wear or fragment during usage, a process that is typically referred to as "coating spallation" or "spallation". Spallation may result in the formation and growth of uncoated or exposed areas at discrete areas or patches on the surface of the affected component. These unprotected areas experience higher temperatures and, thus, are subject to more rapid deterioration, including the premature formation of fatigue cracks and other defects. In combustion turbine engines, coating spallation is a particular concern for turbine rotor blades and components within the combustor, such as the transition piece. Early detection of coating spallation may allow an operator to take corrective action before the component becomes completely damaged from the increased thermal strain.

While the operators of combustion turbine engines want to avoid using worn-out or compromised components that risk failing during operation, they also have a competing interests of not prematurely replacing components before their useful life is exhausted. That is, operators want to exhaust the useful life of each component, thereby minimizing part costs while also reducing the frequency of engine outages for part replacements to occur. Accordingly, accurate crack detection and/or coating spallation in engine components is a significant industry need. However, conventional methods generally require regular visual inspection of parts. While useful, visual inspection is both time-consuming and requires the engine be shutdown for a prolonged period.

The ability to monitor components in the hot-gas path while the engine operates for the formation of cracks and the spallation of protective coatings remains a longstanding need. What is needed is a system by which crack formation and spallation may be monitored while the engine operates so that necessary action may be taken before a failure event occurs or significant component damage is realized. Such a system also may extend the life of components as the need for part replacement may be based on actual, measured wear instead of what is anticipated. In addition, such a system would decrease the need or frequency of performing evaluations, such as visual inspections, that require engine shutdown. To the extent that these objectives may be achieved in a cost-effective manner, efficiency would be enhanced and industry demand would be high.

BRIEF DESCRIPTION OF THE INVENTION

The present invention, thus, describes system for detecting defects in a combustion duct of a combustion system of a combustion turbine engine while the combustion turbine engine operates, wherein, the combustion duct comprises an inner surface, which, during operation, is exposed to the combustion gases of the hot-gas flowpath. In one embodiment, the system includes: an insulator coating disposed on the inner surface of the combustion duct; a first electrode that is electrically connected to the combustion duct; a second electrode that resides within the hot-gas flowpath; means for inducing a voltage across the first electrode and the second electrode; and means for detecting current flowing between the first electrode and the second electrode.

The present invention further describes a method for detecting defects in a combustion duct of a combustion system of a combustion turbine engine while the combustion turbine engine operates, wherein the combustion duct comprises an inner surface, which, during operation, is exposed to the combustion gases of the hot-gas flowpath. In one embodiment, the method includes the steps of: providing a first electrode that is electrically connected to the combustion duct; providing a second electrode that resides within the hot-gas flowpath and within or in proximity to the combustion duct; applying a voltage across the first electrode and the second electrode; and detecting current flowing between the first electrode and the second electrode.

These and other features of the present application will become apparent upon review of the following detailed description of the preferred embodiments when taken in conjunction with the drawings and the appended claims.

BRIEF DESCRIPTION OF THE DRAWINGS

These and other features of this invention will be more completely understood and appreciated by careful study of the following more detailed description of exemplary embodiments of the invention taken in conjunction with the accompanying drawings, in which.

DETAILED DESCRIPTION OF THE INVENTION

Figure 1:
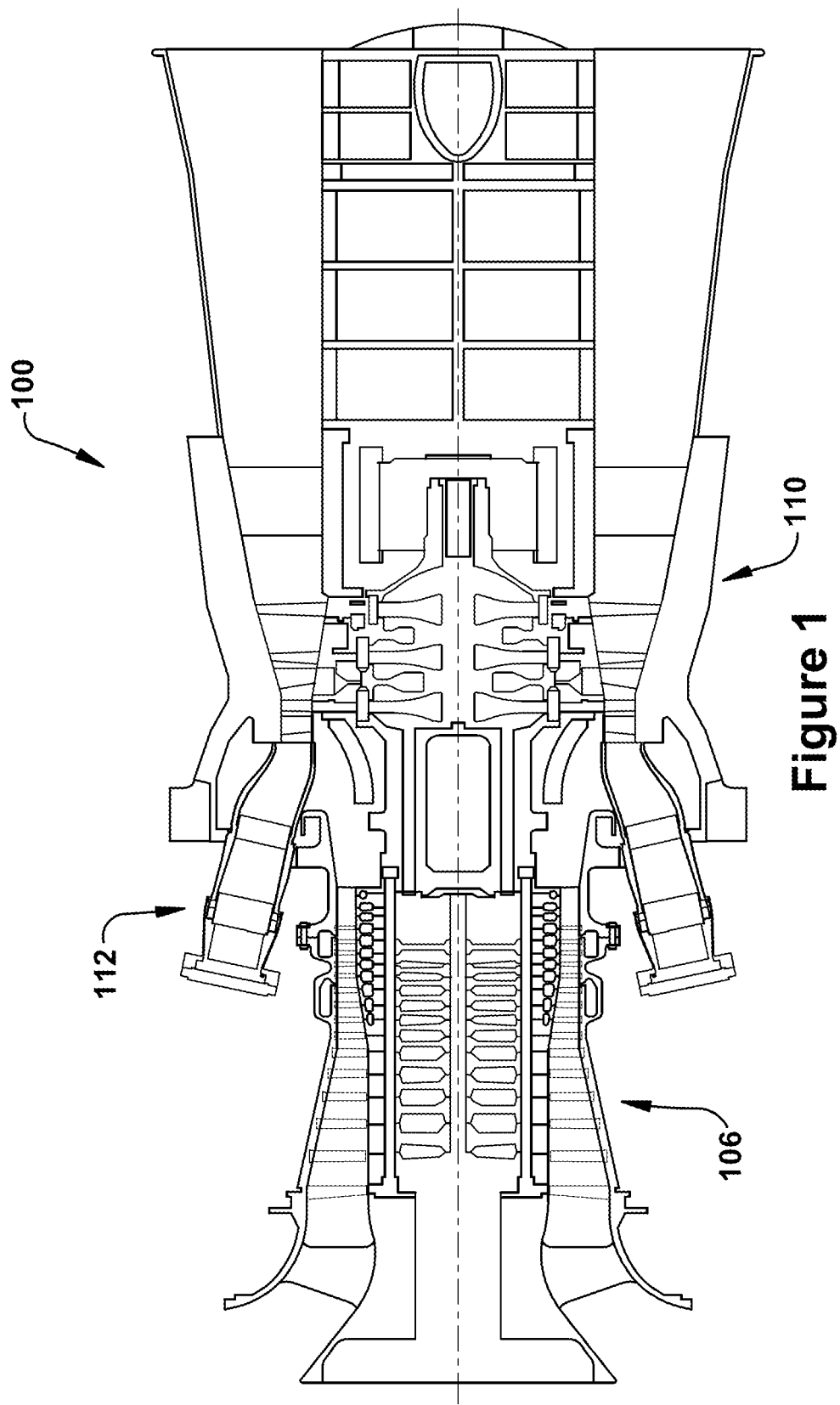
FIG. 1 is a schematic representation of an exemplary turbine engine in which embodiments of the present application may be used.

Referring now to the figures, FIG. 1 illustrates a schematic representation of a gas turbine engine 100 in which embodiments of the present invention may be employed. In general, gas turbine engines operate by extracting energy from a pressurized flow of hot gas that is produced by the combustion of a fuel in a stream of compressed air. As illustrated in FIG. 1, gas turbine engine 100 may be configured with an axial compressor 106 that is mechanically coupled by a common shaft or rotor to a downstream turbine section or turbine 110, and a combustion system 112, which, as shown, is a can combustor that is positioned between the compressor 106 and the turbine 110.

Figure 2:
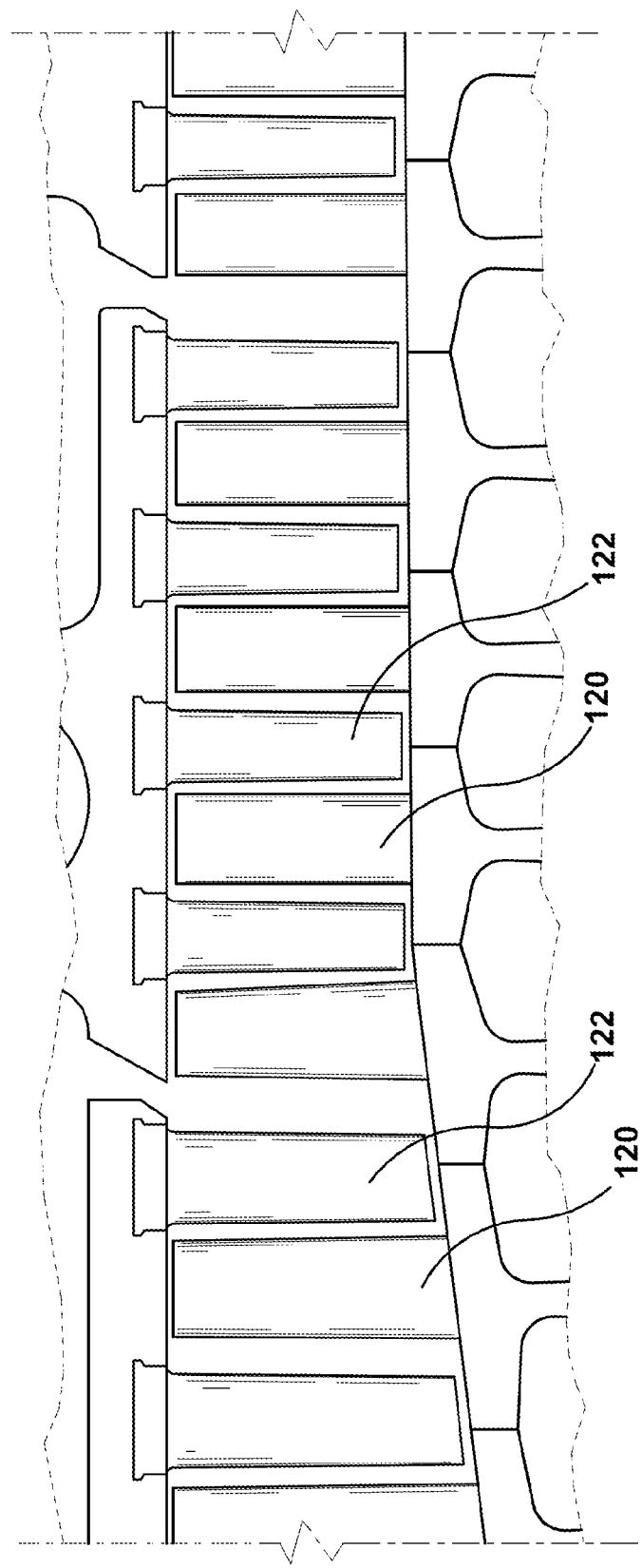
FIG. 2 is a sectional view of an exemplary compressor that may be used in the gas turbine engine of FIG. 1.

FIG. 2 illustrates a view of an axial compressor 106 that may be used in gas turbine engine 100. As shown, the compressor 106 may include a plurality of stages. Each stage may include a row of compressor rotor blades 120 followed by a row of compressor stator blades 122. Thus, a first stage may include a row of compressor rotor blades 120, which rotate about a central shaft, followed by a row of compressor stator blades 122, which remain stationary during operation. The compressor stator blades 122 generally are circumferentially spaced one from the other and fixed about the axis of rotation. The compressor rotor blades 120 are circumferentially spaced about the axis of the rotor and rotate about the shaft during operation. As one of ordinary skill in the art will appreciate, the compressor rotor blades 120 are configured such that, when spun about the shaft, they impart kinetic energy to the air or working fluid flowing through the compressor 106. As one of ordinary skill in the art will appreciate, the compressor 106 may have many other stages beyond the stages that are illustrated in FIG. 2. Each additional stage may include a plurality of circumferential spaced compressor rotor blades 120 followed by a plurality of circumferentially spaced compressor stator blades 122.

Figure 3:
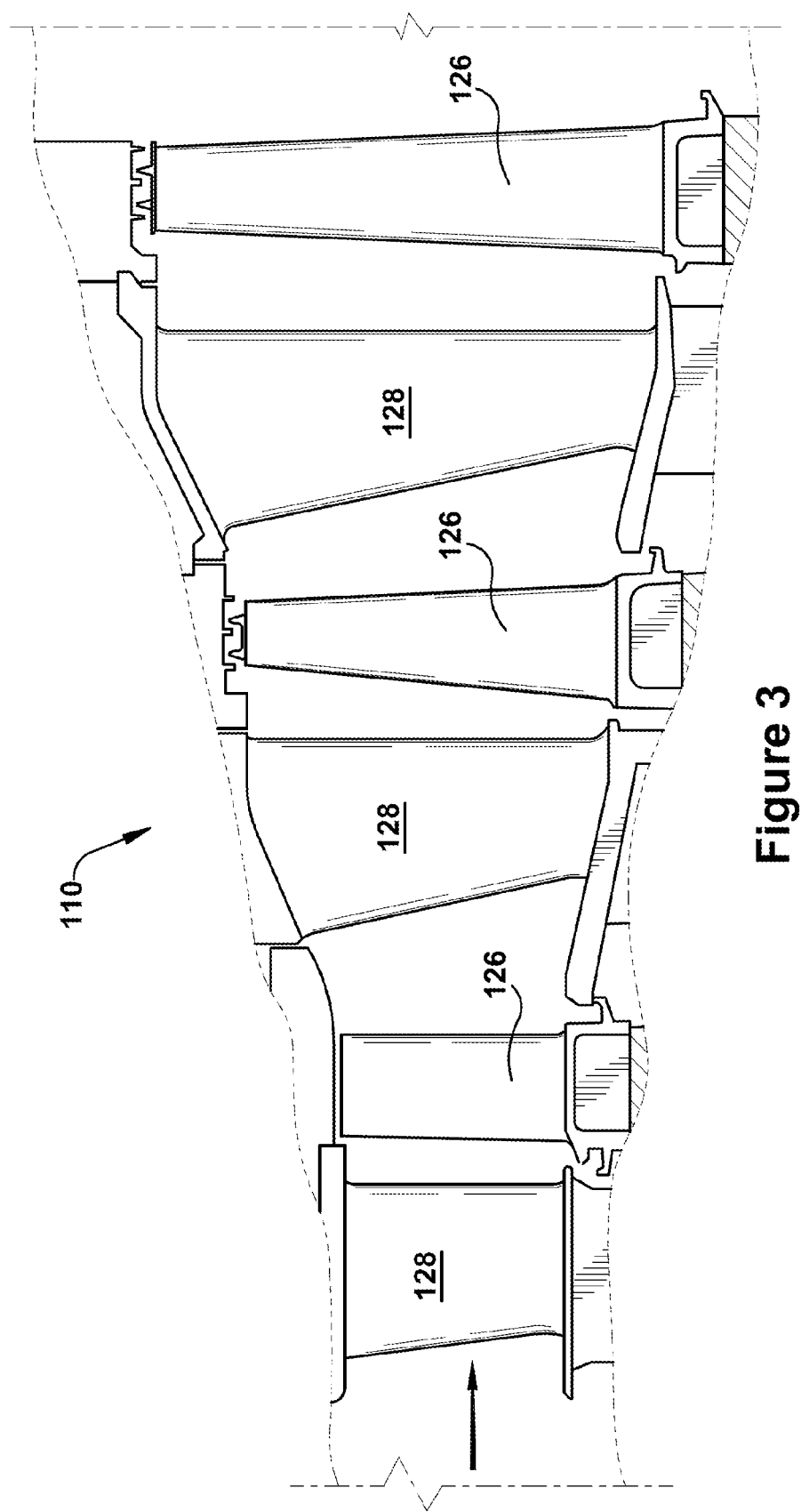
FIG. 3 is a sectional view of an exemplary turbine that may be used in the gas turbine engine of FIG. 1.

FIG. 3 illustrates a partial view of an exemplary turbine section or turbine 110 that may be used in a gas turbine engine 100. The turbine 110 may include a plurality of stages. Three exemplary stages are illustrated, but more or less stages may be present in the turbine 110. A first stage includes a plurality of turbine buckets or turbine rotor blades 126, which rotate about the shaft during operation, and a plurality of nozzles or turbine stator blades 128, which remain stationary during operation. The turbine stator blades 128 generally are circumferentially spaced one from the other and fixed about the axis of rotation. The turbine rotor blades 126 may be mounted on a turbine wheel (not shown) for rotation about the shaft (not shown). A second stage of the turbine 110 is also illustrated. The second stage similarly includes a plurality of circumferentially spaced turbine stator blades 128 followed by a plurality of circumferentially spaced turbine rotor blades 126, which are also mounted on a turbine wheel for rotation. A third stage also is illustrated, and similarly includes a plurality of circumferentially spaced turbine stator blades 128 and turbine rotor blades 126. It will be appreciated that the turbine stator blades 128 and turbine rotor blades 126 lie in the hot gas path of the turbine 110. The direction of flow of the hot gases through the hot gas path is indicated by the arrow. As one of ordinary skill in the art will appreciate, the turbine 110 may have many other stages beyond the stages that are illustrated in FIG. 3. Each additional stage may include a plurality of circumferential spaced turbine stator blades 128 followed by a plurality of circumferentially spaced turbine rotor blades 126.

A gas turbine engine of the nature described above may operate as follows. The rotation of compressor rotor blades 120 within the axial compressor 106 compresses a flow of air. In the combustor 112, as described in more detail below, energy is released when the compressed air is mixed with a fuel and ignited. The resulting flow of hot gases from the combustor 112 then may be directed over the turbine rotor blades 126, which may induce the rotation of the turbine rotor blades 126 about the shaft, thus transforming the energy of the hot flow of gases into the mechanical energy of the rotating shaft. The mechanical energy of the shaft may then be used to drive the rotation of the compressor rotor blades 120, such that the necessary supply of compressed air is produced, and also, for example, a generator to produce electricity.

Before proceeding further, it will be appreciated that in order to communicate clearly the present invention, it will become necessary to select terminology that refers to and describes certain parts or machine components of a turbine engine and related systems, particularly, the combustor system. Whenever possible, industry terminology will be used and employed in a manner consistent with its accepted meaning. However, it is meant that any such terminology be given a broad meaning and not narrowly construed such that the meaning intended herein and the scope of the appended claims is unreasonably restricted. Those of ordinary skill in the art will appreciate that often a particular component may be referred to using several different terms. In addition, what may be described herein as a single part may include and be referenced in another context as consisting of several component parts, or, what may be described herein as including multiple component parts may be fashioned into and, in some cases, referred to as a single part. As such, in understanding the scope of the invention described herein, attention should not only be paid to the terminology and description provided, but also to the structure, configuration, function, and/or usage of the component, as provided herein.

In addition, several descriptive terms may be used regularly herein, and it may be helpful to define these terms at this point. These terms and their definition given their usage herein is as follows. The term "rotor blade", without further specificity, is a reference to the rotating blades of either the compressor or the turbine, which include both compressor rotor blades and turbine rotor blades. The term "stator blade", without further specificity, is a reference the stationary blades of either the compressor or the turbine, which include both compressor stator blades and turbine stator blades. The term "blades" will be used herein to refer to either type of blade. Thus, without further specificity, the term "blades" is inclusive to all type of turbine engine blades, including compressor rotor blades, compressor stator blades, turbine rotor blades, and turbine stator blades. Further, as used herein, "downstream" and "upstream" are terms that indicate a direction relative to the flow of a fluid, such as the working fluid through the turbine. As such, the term "downstream" refers to a direction that generally corresponds to the direction of the flow of working fluid, and the term "upstream" generally refers to the direction that is opposite of the direction of flow of working fluid. The terms "forward" or "leading" and "aft" or "trailing" generally refer to relative position in relation to the forward end and aft end of the turbine engine (i.e., the compressor is the forward end of the engine and the end having the turbine is the aft end). At times, which will be clear given the description, the terms "leading" and "trailing" may refer to the direction of rotation for rotating parts. When this is the case, the "leading edge" of a rotating part is the edge that leads in the rotation and the "trailing edge" is the edge that trails.

The term "radial" refers to movement or position perpendicular to an axis. It is often required to described parts that are at differing radial positions with regard to an axis. In this case, if a first component resides closer to the axis than a second component, it may be stated herein that the first component is "radially inward" or "inboard" of the second component. If, on the other hand, the first component resides further from the axis than the second component, it may be stated herein that the first component is "radially outward" or "outboard" of the second component. The term "axial" refers to movement or position parallel to an axis. Finally, the terms "circumferential" or "angular position" refers to movement or position around an axis.

Figure 4:
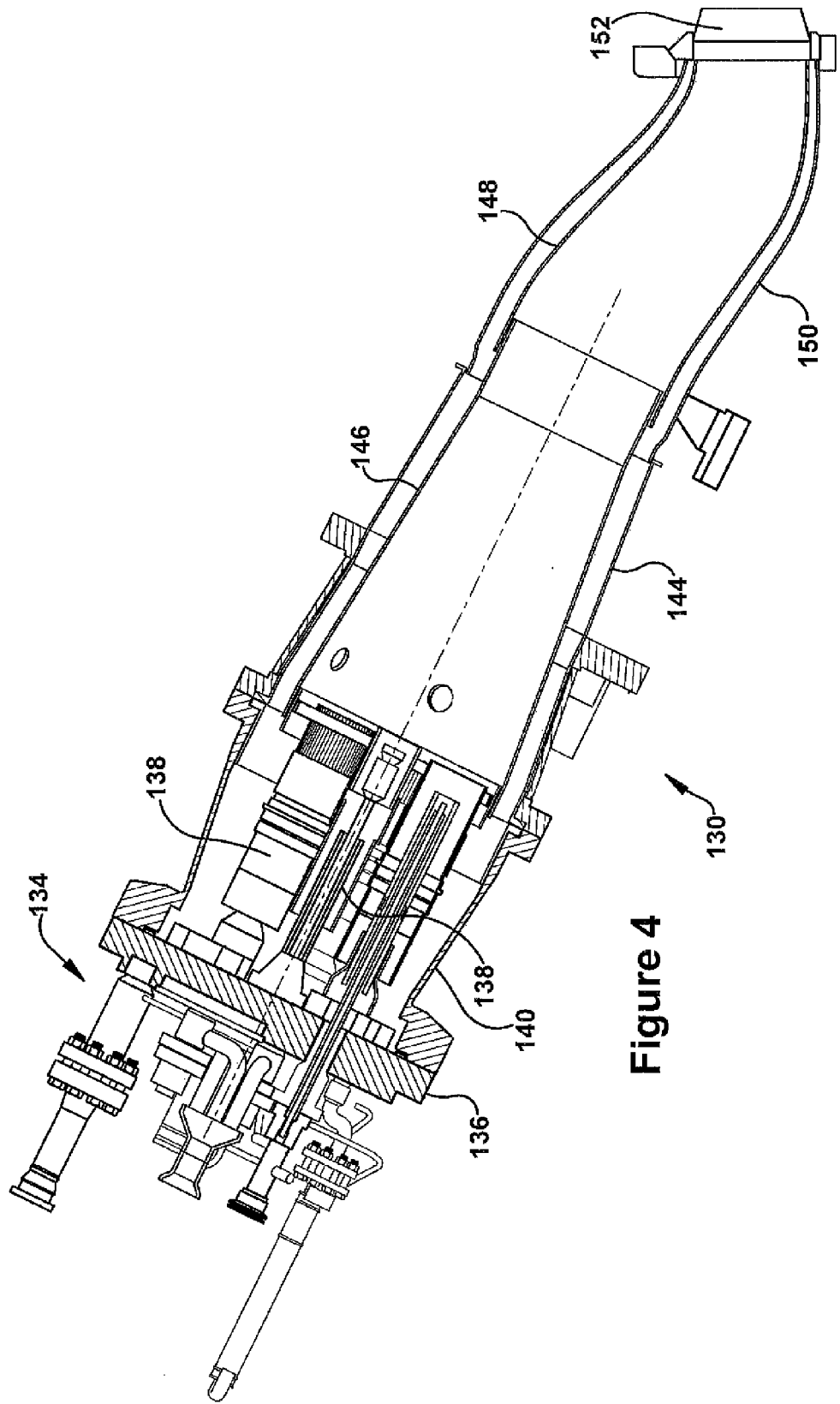
FIG. 4 is a sectional view of an exemplary combustor that may be used in the gas turbine engine of FIG. 1 and in which the present invention may be employed.
Figure 5:
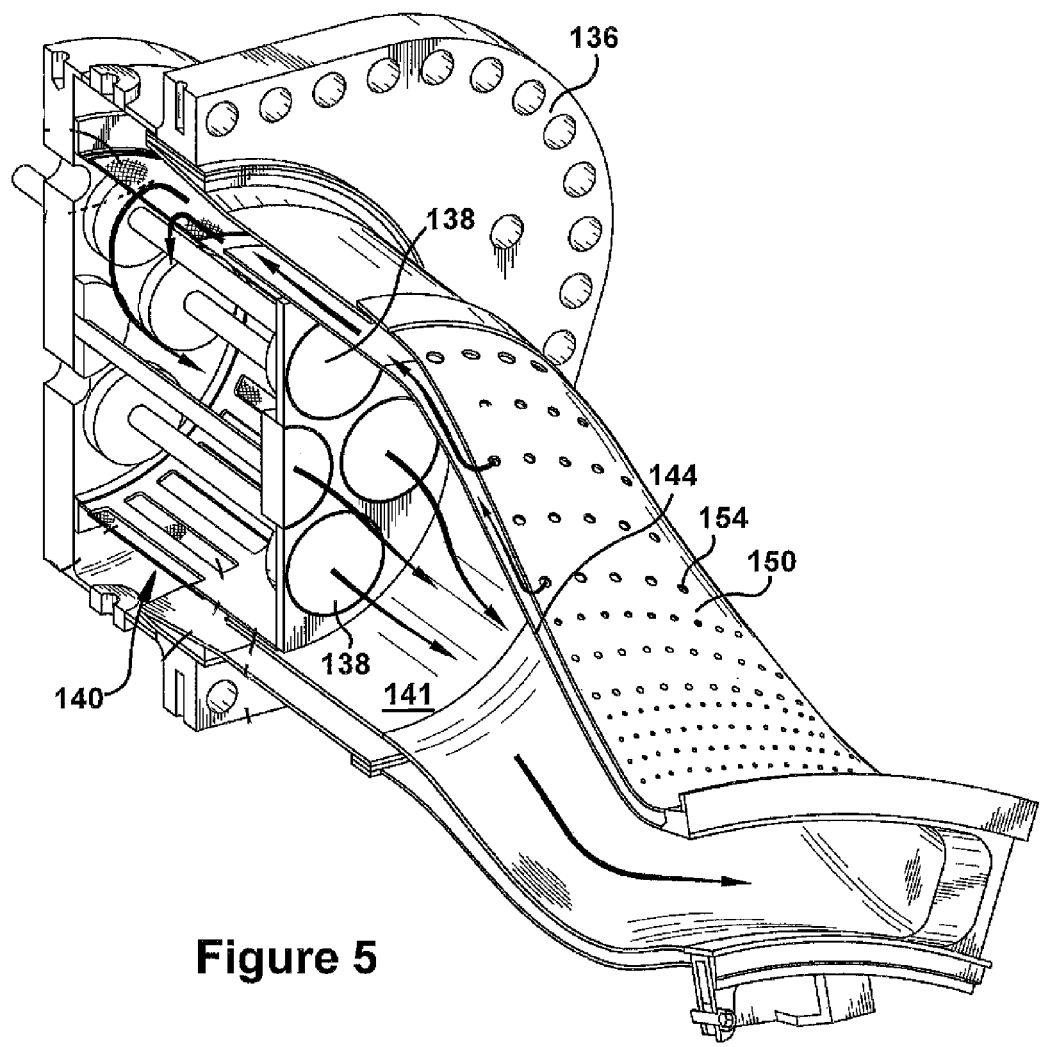
FIG. 5 is a perspective cutaway of an exemplary combustor in which embodiments of the present invention may be employed.

FIGS. 4 and 5 illustrates an exemplary combustor 130 that may be used in a gas turbine engine and in which embodiments of the present invention may be used. As one of ordinary skill in the art will appreciate, the combustor 130 may include a headend 134, which generally includes the various manifolds that supply the necessary air and fuel to the combustor, and an end cover 136. A plurality of fuel lines 137 may extend through the end cover 136 to fuel nozzles or fuel injectors 138 that are positioned at the aft end of a forward case or cap assembly 140. It will be appreciated that the cap assembly 140 generally is cylindrical in shape and fixed at a forward end to the end cover 136.

In general, the fuel injectors 138 bring together a mixture of fuel and air for combustion. The fuel, for example, may be natural gas and the air may be compressed air (the flow of which is indicated in FIG. 4 by the several arrows) supplied from the compressor. As one of ordinary skill in the art will appreciate, downstream of the fuel injectors 138 is a combustion chamber 141 in which the combustion occurs. The combustion chamber 141 is generally defined by a liner 146, which is enclosed within a flow sleeve 144. Between the flow sleeve 144 and the liner 146 an annulus is formed. From the liner 146, a transition piece 148 transitions the flow from the circular cross section of the liner to an annular cross section as it travels downstream to the turbine section (not shown in FIG. 4). A transition piece impingement sleeve 150 (hereinafter "impingement sleeve 150") may enclose the transition piece 148, also creating an annulus between the impingement sleeve 150 and the transition piece 148. At the downstream end of the transition piece 148, a transition piece aft frame 152 may direct the flow of the working fluid toward the airfoils that are positioned in the first stage of the turbine 110. It will be appreciated that the flow sleeve 144 and the impingement sleeve 150 typically have impingement apertures (not shown in FIG. 4) formed therethrough which allow an impinged flow of compressed air from the compressor 106 to enter the cavities formed between the flow sleeve 144 and the liner 146 and between the impingement sleeve 150 and the transition piece 148. The flow of compressed air through the impingement apertures convectively cools the exterior surfaces of the liner 146 and the transition piece 148.

Figure 6:
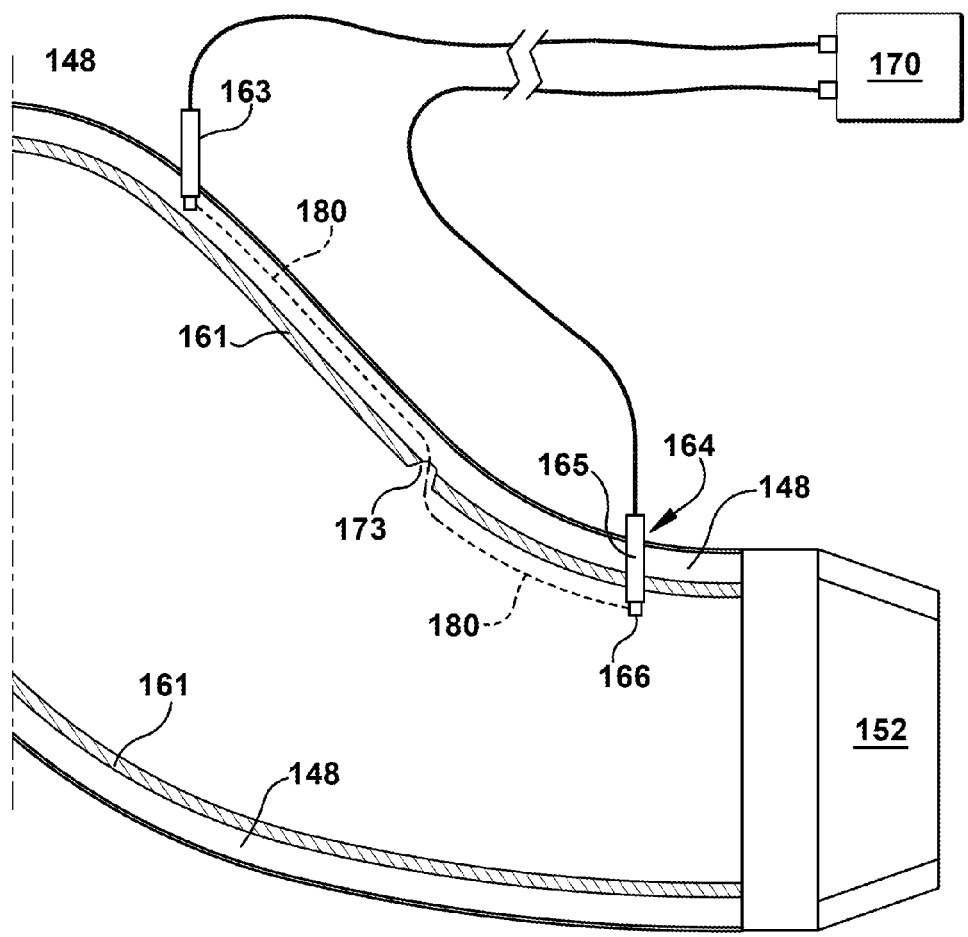
FIG. 6 illustrates cross-sectional view of a transition piece and a system for monitoring material defects according to an exemplary embodiment of the present invention.

Referring now to FIG. 6, a system for monitoring material defects according to an exemplary embodiment of the present invention is provided. This exemplary embodiment is described in relation to usage within the transition piece 148 of the combustion system. As provided below, however, it will be appreciated that is description is exemplary only and that the present invention may be used with other ducts through which combustion gases or hot gases flow, including the liner 146. According to the present invention, the interior surface of the transition piece 148 may be coated with an insulator coating 161. In some embodiments, the insulator coating 161 may comprise a thermal barrier coating. In particular, a zirconia oxide thermal barrier coating may be used in certain preferred environments. However, the present invention is not limited to this type of coating. Any coating that, relatively speaking, provides electrical insulation may be used. That is, any coating that is suitable for use in the turbine environment and proves to be less electrically conductive as the underlying structure of the transition piece 148 or combustion duct may be used. It will be appreciated that the insulator coating may also have an electrical conductivity that is less than the combustion gases that, during engine operation, flow through the transition piece 148. In some embodiments, the insulator coating may consist of ceramic materials, corrosion coatings, or combustion products.

As shown, a first electrode 163 may be electrically connected to the transition piece 148. It will be appreciated that the transition piece 148 may be metallic and have a high electrical conductivity. A second electrode 164 may be positioned such that it is electrically exposed to the hot-gas path (and not connected to the transition piece 148). One manner in which this may be done is to have the second electrode 164 pass through the transition piece 148 but be electrically insulated from the transition piece 148 by an electrically insulating material or structure 165, while also having a conducting tip 166 that is exposed to the hot-gas path, as shown in FIG. 6. As such, the second electrode 164 may be positioned, at least in part, such that it is exposed to the hot-gas flow path and in proximity to the first electrode 163. In an exemplary embodiment, the second electrode 164 may be positioned downstream of the first electrode 163 and/or downstream (or toward the downstream end) of the transition piece 148. The second electrode 164 may be constructed of materials capable of withstanding the rigors of the hot-gas flow path. For example, the conducting tip 166 of the second electrode 164 may be made of copper, silver, manganese, silicon or other suitable materials.

The first electrode 163 and the second electrode 164, as indicated in FIG. 6, may be connected to a control unit 170. The control unit 170 may include a voltage source that is configured to apply a voltage across the two electrodes 163, 164. The voltage source may include any conventional systems or equipment having a power or voltage supply. The control unit 170 also may include an amp meter or similar instrument for determining or detecting if current flows between the two electrodes 163, 164 and/or measuring the level of current flowing between the two electrodes 163, 164.

During normal operation, it will be appreciated that there will be no or relatively little current detected by the control unit 170 as flowing between the two electrodes 163, 164. This is due to electrical insulation of the insulator coating 161 that covers the inside surface of the transition piece 148. That is, the insulator coating 161 may separate the voltage being applied to the transition piece 148 from the hot gases of the flowpath. However, when a crack originates at any location along the interior of the transition piece 148, it will be appreciated that it may undermine the insulator coating 161 and eventually cause a defect 173, as indicated in FIG. 6. More specifically, the crack may eventually cause spallation of the thermal barrier coating (or other insulator coating) such that an exposed patch or portion or area of the more electrically conductive surface of the transition piece 148 is exposed to the hot gases of the flowpath during engine operation.

It will be appreciated by those of ordinary skill in the art that the combustion gases of the hot-gas flowpath are relatively electrically conducting and that an electric circuit 180 may form when the surface of the transition piece 148 is exposed. That is, the hot gases may conduct electricity between the exposed surface of the transition piece 148 (which has become exposed because of the erosion or spallation caused by a defect 173 within the transition piece 148) and the conducting tip 166 of the second electrode 164. As such, the control unit 170 will detect that current is flowing between the two electrodes 163, 164 and that the electric circuit 180 has formed. In exemplary embodiments, the detection of the circuit 180 may cause the system to provide a warning notification that a defect 173 is likely and/or that corrective action should be taken. The sensitivity of the system may be adjusted by using different voltages or requiring certain current thresholds be satisfied before a warning notification is issued.

In an alternative embodiment, a current may be observed as flowing between the two electrodes 163, 164 during normal operation, which becomes elevated when a defect 173 occurs. This may be due to the fact that certain types of protective insulator coatings are electrically conductive (or, at least, more electrically conductive than other types of coatings). Accordingly, in this case, during normal operation, it will be appreciated that there will be a level of current observed by the control unit 170 between the two electrodes 163, 164. However, when a crack originates that undermines the insulator coating causing spallation of the coating or simple erosion of the insulator coating causes a portion of the more electrically conductive surface of the transition piece 148 to become exposed to the combustion gases of the hot-gas flow path, an increased level of current flowing between the two electrodes 163, 164 will be observed by the control unit 170. In this embodiment, the observation of the increase in current provides the warning signal for a defect 138. As before, the detection of the increased current through circuit 180 may cause the system to provide a warning notification that a defect 173 is likely and/or that corrective action should be taken. The sensitivity of the system may be adjusted by using different voltages or requiring certain current thresholds or, in the case of this embodiment, thresholds indicating a certain level of current change be satisfied before a warning notification is issued.

In some embodiments, the conductivity of the hot gases of the flow path may be increased by doping the fuel with a conductive material or injecting a conductive media in to the flowpath of compressed air within the compressor of the engine. It will be appreciated that the injection of a conductive material may enhance the level of current flowing between the electrodes and increase the accuracy of the detection system. In some embodiments, the injection of a conductive doping material may be done periodically during test cycles in which tests for defects (i.e., crack formation or coating spallation) are performed. As stated, this temporary measure may increase the accuracy of detection of defects. In addition, the size of the defect 173 may be determined by calibrating the system with the magnitude of current flow through the formed electrical circuit 180 given the voltage applied and prior defect sizes as well as other relevant conditions (i.e., whether a doping agent is present, etc.). For example, higher current levels will be indicative of bigger defect sizes. Threshold current levels may be set that indicate defects of certain sizes.

In the absence of a crack forming along the interior surface of the transition piece, simple erosion or spallation of the electrical insulting coating 161 also may cause a defect 173 that exposes the metallic surface of the transition piece 148 to the hot gases of the flow path. That is, spallation or erosion of the thermal barrier coating regularly occurs without the formation of a transition piece crack. Whatever the case, the exposed surface that results will cause the formation of the electrical circuit 180 between the two electrodes 163, 164 and, thereby, cause the detection of a current by the control unit 170 that indicates such a defect is present. The spallation may be caused by the wearing away or erosion of the insulator coating 161 within the transition piece 148. In this case, the system may prevent the deterioration of the exposed material and/or subsequent the formation of cracks or more serious defect by providing a warning of the defect 173. It will be appreciated that, absent corrective action, spallation may result in increased thermal strain to interior surface of the transition piece 148 and/or material deterioration, which may cause catastrophic system failures without corrective action.

Testing has confirmed the function of the present invention. For example, in one test, two electrodes were positioned within the transition piece of a combustor in a manner consistent with the description above. A voltage source was connected to the electrodes and approximately 5V was applied across them. A threshold current (i.e., the indicator current) of approximately 1.25 microamps was set. The test results showed that, given these parameters, the detectable spallation size (i.e., the area of transition piece surface exposed to the hot gases) was approximately 0.5 inches-squared. That is, the test results showed that a defect that resulted in exposing at least 0.5 inches-squared of the inner surface of the transition piece caused the threshold or indicator current to be exceeded. The parameters, of course, may be adjusted depending on the characteristics of the system and the desired sensitivity, as one of ordinary skill in the art will appreciate.

It will be appreciated by one of ordinary skill in the art that the above application is exemplary and that these same methods of detecting defects in other ducts through which combustion gases are directed. For example, the same methods as described above in relation to the transition piece 148 may be applied in similar fashion to the liner 146 of the combustion system, or, for that matter, in other similar ducts. As such, when reference is made within the appended claims to a "combustion duct", it will be appreciated that this includes both the transition piece 148 and the liner 146. Also, as stated, such a reference may include any other similar duct through which combustion gases flow.

It will be appreciated that by monitoring crack formation and coating spallation while the engine operates may reduce the need for regular visual inspections, which may also reduce engine down time. As will be appreciated, typically the transition piece 148 and the liner 146 are not inspected until the combustion system undergoes a diagnostic check after several thousands of hours of operation. Monitoring for crack formation and spallation while the engine operates may detect the formation of a significant defect that otherwise would have gone unnoticed until this inspection occurs. Depending on the severity of the defect, significant damage may occur if the engine continues to operate and corrective action is not taken, particularly if a failure liberates pieces of the transition piece or liner or other such duct that cause damage to downstream components. Such an event may be avoided if the real-time monitoring capabilities of the present invention are available.

As one of ordinary skill in the art will appreciate, the many varying features and configurations described above in relation to the several exemplary embodiments may be further selectively applied to form the other possible embodiments of the present invention. For the sake of brevity and taking into account the abilities of one of ordinary skill in the art, all of the possible iterations is not provided or discussed in detail, though all combinations and possible embodiments embraced by the several claims below or otherwise are intended to be part of the instant application. In addition, from the above description of several exemplary embodiments of the invention, those skilled in the art will perceive improvements, changes and modifications. Such improvements, changes and modifications within the skill of the art are also intended to be covered by the appended claims. Further, it should be apparent that the foregoing relates only to the described embodiments of the present application and that numerous changes and modifications may be made herein without departing from the spirit and scope of the application as defined by the following claims and the equivalents thereof.

We claim:

1. A system for detecting defects in a combustion duct of a combustion system of a combustion turbine engine while the combustion turbine engine operates, wherein, the combustion duct comprises an inner surface, which, during operation, is exposed to the combustion gases of the hot-gas flowpath, the system comprising:
    an insulator coating disposed on the inner surface of the combustion duct;
    a first electrode that is electrically connected to the combustion duct;
    a second electrode that resides within the hot-gas flowpath;
    means for inducing a voltage across the first electrode and the second electrode; and
    means for detecting current flowing between the first electrode and the second electrode;
    wherein the second electrode extends through the combustion duct and comprises insulating structure that insulates the second electrode from being electrically connected to the combustion duct;
    wherein the second electrode comprises a conducting tip at a distal end that projects into the hot-gas flowpath through the combustion duct;
    wherein the second electrode comprises a position that is downstream of at least a majority of the combustion duct to which the first electrode is electrically connected;
    wherein the insulator coating comprises a thermal barrier coating; and
    wherein the combustion duct comprises one of a transition piece and a liner.

2. The system according to claim 1, wherein the second electrode comprises a position that is in proximity to a downstream end of the combustion duct to which the first electrode is electrically connected;
    wherein the second electrode, during operation, is electrically connected to the combustion gases flowing through the combustion duct during operation of the combustion turbine engine.

3. The system according to claim 1, wherein, during operation, the hot-gas flowpath of the combustion turbine engine comprises an electrically conductive doping agent;
    wherein the electrically conductive doping agent is injected into the hot-gas flowpath at predetermined testing intervals; and
    wherein the electrically conductive doping agent is injected into the hot-gas flowpath at a position that is upstream of the combustion duct.

4. The system according to claim 1, further comprising a control unit;
    wherein the control unit comprises a voltage source that is configured to apply a predetermined level of voltage across the first electrode and the second electrode; and
    wherein the control unit comprises an amp meter that is configured to detect current flowing between the first electrode and the second electrode.

5. The system according to claim 4, wherein the control unit comprises an amp meter that is configured to detect a level of current flowing between the first electrode and the second electrode; and
    wherein the control unit is configured to determine whether the detected current level between the first electrode and the second electrode exceeds a threshold current level.

6. The system according to claim 5, wherein the first electrode, the second electrode, and the control unit are configured such that when the insulator coating comprises a desired level of coverage over the inner surface of the combustion duct, the predetermined voltage level applied across the first electrode and the second electrode fails to induce the detected current level between the first electrode and the second electrode to exceed the threshold current level.

7. The system according to claim 5, wherein the first electrode, the second electrode, and the control unit are configured such that:
    during a first operating condition, the detected current level between the first electrode and the second electrode does not exceed the threshold current level; and
    during a second operating condition, the detected current level between the first electrode and the second electrode exceeds the threshold current level;
    wherein the second operating condition comprises an operating conditioning in which a defect is present in the insulator coating.

8. The system according to claim 7, wherein the defect comprises an exposed area of a predetermined size on the inner surface of the combustion duct, the exposed area comprising an area that is substantially no longer covered by the insulator coating; and
    wherein the predetermined size of the exposed area corresponds to an area of exposure at which the predetermined voltage level induces the detected current level to exceed the threshold current level.

9. The system according to claim 7, wherein the defect comprises one of spallation of the insulator coating and crack formation within the inner surface of the combustion duct.

10. The system according to claim 7, wherein the first operating condition comprises an operating condition in which a desired portion of the inner surface of the combustion duct is covered by the insulator coating; and
    wherein the control unit is configured to issue a warning notification when the second operating condition occurs.

11. The system according to claim 10, wherein:
the insulator coating comprises an electrical conductivity that is less than the electrical conductivity of the combustion duct;
the insulator coating comprises an electrical conductivity that is less than the approximate electrical conductivity of the combustion gases flowing through the combustion duct during operation of the combustion turbine engine; and
the desired portion comprises substantially all of the inner surface of the combustion duct.

12. A method for detecting defects in a combustion duct of a combustion system of a combustion turbine engine while the combustion turbine engine operates, wherein the combustion duct comprises an inner surface, which, during operation, is exposed to the combustion gases of the hot-gas flowpath, the method comprising the steps of:
providing a first electrode that is electrically connected to the combustion duct;
providing a second electrode that resides within the hot-gas flowpath and within or in proximity to the combustion duct;
applying a voltage across the first electrode and the second electrode; and
detecting current flowing between the first electrode and the second electrode;
wherein the second electrode comprises a conducting tip at a distal end that projects into the hot-gas flowpath through the combustion duct;
wherein the second electrode comprises a position that is in proximity to a downstream end of the combustion duct to which the first electrode is electrically connected;
wherein the insulator coating comprises a thermal barrier coating; and
wherein the combustion duct comprises one of a transition piece and a liner.

13. The method according to claim 12, further comprising the step of coating the inner surface of the combustion duct with an insulator coating;
wherein:
the insulator coating comprises an electrical conductivity that is less than the electrical conductivity of the combustion duct; and
the insulator coating comprises an electrical conductivity that is less than the approximate electrical conductivity of the combustion gases flowing through the combustion duct during operation of the combustion turbine engine.

14. The method according to claim 13, further comprising the steps of:
detecting a level of current flowing between the first electrode and the second electrode; and
determining whether the detected current level exceeds a threshold current level.

15. The method according to claim 14, wherein the threshold current level corresponds to a threshold above which detected current levels comprise a high probability of being caused by a defect in the insulator coating.

16. The method according to claim 15, wherein the defect comprises an exposed area of predetermined size on the inner surface of the combustion duct, the exposed area comprising an area that is substantially no longer covered by the insulator coating; and
wherein the predetermined size of the exposed area corresponds to a size at which the predetermined voltage level induces the detected current level to exceed the threshold current level.

17. The method according to claim 15, wherein detected current levels that do not exceed the threshold current level correspond to current levels that occur when a desired portion of the inner surface of the combustion duct remains covered by the insulator coating;
further comprising the step of issuing a warning notification when the detected current level exceeds the threshold current level.

18. The method according to claim 12, further comprising the step of injecting an electrically conductive doping agent into the hot-gas flowpath at a position that is upstream from the combustion duct.

19. The method according the claim 18, wherein the electrically conductive doping agent is configured to increase the electrical conductivity of the combustion gases flowing through the hot-gas flowpath during operation of the combustion turbine engine.

20. The method according to claim 19, wherein the electrically conductive doping agent is injected periodically, the periods of injection corresponding to a desired testing schedule.

* * * * *